(12) United States Patent
Grecco et al.

(10) Patent No.: US 9,017,414 B2
(45) Date of Patent: Apr. 28, 2015

(54) TRIAL IMPLANT AND METHOD OF USE

(75) Inventors: John Jude Grecco, Butler, NJ (US);
Troy Allen McMillen, Milford, PA (US)

(73) Assignee: Howmedica Osteonics Corp., Mahwah, NJ (US)

( * ) Notice: Subject to any disclaimer, the term of this patent is extended or adjusted under 35 U.S.C. 154(b) by 1191 days.

(21) Appl. No.: 12/313,266

(22) Filed: Nov. 18, 2008

(65) Prior Publication Data
US 2010/0125337 A1    May 20, 2010

(51) Int. Cl.
*A61F 2/38*  (2006.01)
*A61F 2/46*  (2006.01)
*A61F 2/30*  (2006.01)

(52) U.S. Cl.
CPC .............. *A61F 2/4684* (2013.01); *A61F 2/38* (2013.01); *A61F 2/3859* (2013.01); *A61F 2/3877* (2013.01); *A61F 2/389* (2013.01); *A61F 2002/30616* (2013.01); *A61F 2002/4619* (2013.01)

(58) Field of Classification Search
USPC ................................ 623/17.16, 20.14; 606/99
See application file for complete search history.

(56) References Cited

U.S. PATENT DOCUMENTS

| 5,683,469 | A  | * | 11/1997 | Johnson et al. | ............ | 623/20.32 |
| 5,702,463 | A  | * | 12/1997 | Pothier et al. | ............ | 623/20.32 |
| 6,916,341 | B2 |   | 7/2005  | Rolston        |              |           |
| 2004/0064191 | A1 |   | 4/2004 | Wasielewski   |              |           |
| 2005/0131543 | A1 | * | 6/2005 | Benzel et al. | ............ | 623/17.13 |
| 2005/0209703 | A1 | * | 9/2005 | Fell           | ............ | 623/20.33 |
| 2006/0111726 | A1 |   | 5/2006 | Felt et al.   |              |           |
| 2007/0055269 | A1 |   | 3/2007 | Iannarone et al. |          |           |
| 2008/0091211 | A1 | * | 4/2008 | Gately         | ............ | 606/99    |
| 2009/0187246 | A1 | * | 7/2009 | Foley          | ............ | 623/17.16 |

* cited by examiner

*Primary Examiner* — Bruce E Snow
*Assistant Examiner* — Melissa Hoban
(74) *Attorney, Agent, or Firm* — Lerner, David, Littenberg, Krumholz & Mentlik, LLP (57) ABSTRACT

Disclosed is a trial implant having a body and a tab. The body may include a recess and may be sized to closely approximate a permanent implant. The tab may be more durable than the body, and may be disposed within the body and wholly contained within the recess. Also disclosed is a method of performing a trialing procedure including providing a trial implant as described, providing a tool to attach to the tab, inserting the implant onto a resected joint, evaluating and extracting the implant. The same procedure may then be performed with a second implant. The method may further include a tool having an attachment portion that is substantially or wholly contained within the recess. A kit is disclosed including a plurality of trial implants of incrementally different shapes and sizes. The kit may further include a tool. Also disclosed is a method of making the described implant.

34 Claims, 8 Drawing Sheets

TRIAL IMPLANT AND METHOD OF USE

BACKGROUND OF THE INVENTION

The present invention is directed to implants, and more particularly to trial implants that are durable and easy to manipulate.

Orthopedic procedures generally involve the resection of a bone, a trialing step to determine the proper size of a permanent implant, and implantation of the permanent implant. For instance, it has long been known in the art for orthopedic procedures involving the knee to include the resection of one or both tibial condyles, or portions thereof. The resection itself generally entails cutting and removing at least a portion of the proximal end of a tibial condyle and replacing same with a permanent tibial implant, which is typically comprised of a base plate and an insert. This type of knee surgery may be necessitated by a fracture or other deterioration of the tibial bone (as well as corresponding femoral bone). As such, the permanent tibial implant is used to improve or restore the normal functionality of the knee joint.

During the surgical procedure, a surgeon will resect an appropriately sized portion of the proximal tibial condyle to prepare the tibial platform. Often, a cut is made at a specific depth in the distal direction. The resected surface is then prepared to receive the permanent implant typically including both a metal baseplate and a polymeric insert, although certain permanent implants are constructed entirely of either metal or a polymeric material. However, as the size of the patient, the tibial bone, and the resected area can vary greatly from procedure to procedure, the particular size and shape of the permanent implant varies as well. It can often be difficult to determine the exact size and orientation of the permanent tibial implant prior to actually performing the surgical procedure.

In order to more accurately and precisely fit the permanent tibial implant to the resected bone, surgeons may use a set of trial implants which can be inserted and removed during the procedure to determine which provides the best fit according to the resected bone surface. The implant's height, size, orientation, and cooperation with a corresponding femoral bone or implant are some of the many factors taken into consideration when fitting a patient with an implant so as to properly balance the knee and restore same to its original capacity.

Existing trial implants are generally comprised entirely of a polymer or a similar material, so as to save in manufacturing costs. As a surgical tool is often used to attach to and manipulate each insert, the polymeric material of the insert can be easily damaged during the trialing procedure. This can lead to portions of the polymeric material being inadvertently introduced into the body of the patient. Moreover, because sets of trial implants can be reused, individual inserts are often damaged to a point where they are no longer functional and must be replaced before future surgeries can be conducted. It is also common that a set of trial implants is designed to require a dedicated instrument to connect with the inserts. The replacement of certain inserts and the acquisition of a dedicated instrument make these existing sets costly.

Another drawback with existing trial implants is that a surgical tool must attach to the implants on their exterior surfaces, and often times their bearing surfaces. This leads to contact between the surgical tool and the anatomy surrounding the implantation site that may be unintentional, but is often unavoidable. Such contact can cause damage to the surrounding bone and tissue, and furthermore, may hinder a surgeon's ability to adequately position the implant.

Thus, a need exists for a set of one or more trial implants that are more durable and hold up better to repeated use, while at the same time keeping costs associated with manufacturing of same low. A need also exists for a set of one or more trial implants that cooperate with a general or specialized surgical tool such that contact between the tool and the anatomy of the patient is substantially or wholly eliminated.

SUMMARY OF THE INVENTION

A first aspect of the present invention is a trial implant comprising a body and a tab disposed within the body. In accordance with one embodiment of this first aspect, the body may be sized to closely approximate the dimensions of a permanent implant to be surgically implanted. The body may include a continuous edge defining a recess. The body may be composed of a first material, and the tab may be composed of a second material that is more durable than the first material. The tab may extend into the recess.

In accordance with other embodiments of the first aspect, the tab may be wholly contained within the recess. The body of the trial implant may be sized to closely approximate the dimensions of a permanent tibial, femoral, patellar, or any other type of implant. The first material may be a polymeric material and the second material may be a rigid biocompatible material, such as metal. The body may further include a top surface and a bottom surface, which may be a mirror image of the top surface. The top surface may include a top bearing portion, and the bottom surface may include a bottom bearing portion, which may be a mirror image of the top bearing portion. The continuous edge may include upper and lower rounded portions proximal to the top surface and the bottom surface, respectively. In accordance with additional embodiments of the first aspect, the tab may include an attachment means such as a hole, a lip, and/or at least one protrusion. The implant may also be marked with indicia.

A second aspect of the present invention is a method of performing a trialing procedure utilizing the aforementioned trial implant. In accordance with one embodiment of this second aspect, the method may include the steps of providing a trial implant, as described above, providing a tool for attaching to the tab, attaching the tool to the tab, inserting the implant onto a resected joint surface, evaluating the implant with respect to the joint surface, and extracting the implant.

In accordance with other embodiments of the second aspect, the joint may be a knee joint, a hip joint, a shoulder joint, or any other joint in the human body. The method may include the steps of providing a kit including a plurality of implants of incrementally different shapes and sizes, and selecting one of the plurality of implants. The method may further include the steps of selecting a second implant from the plurality of implants, attaching the tool to the tab of the second implant, inserting the second implant onto the resected joint surface, evaluating the second implant with respect to the joint surface, and extracting the second implant. The method may include the step of selecting a permanent implant corresponding to the trial implant. The method may further include utilizing a tool that has an attachment portion that is dimensioned to be substantially contained within the recess. The method may further include utilizing a tool that has an attachment portion that is dimensioned to be wholly contained within the recess such that the attachment portion does not extend beyond the top surface or the bottom surface of the body.

A third aspect of the present invention is a kit comprising a plurality of the aforementioned trial implants of incrementally different shapes and sizes. In accordance with one embodiment of the third aspect, the kit may include a tool having an attachment portion configured for attachment to the portion of the tab disposed in the recess. The attachment portion may be at least a clamping portion or a hooking portion configured to mate with the hole of the tab. The attachment portion may be dimensioned to be substantially contained within the recess of the body. The attachment portion may be dimensioned to be wholly contained within the recess such that the attachment portion does not extend beyond the top surface or the bottom surface of the body.

A fourth aspect of the present invention is a method of making a trial implant. In accordance with one embodiment of this fourth aspect, the method may include the steps of providing a tab having an exposed portion and an enclosed portion and made of a rigid biocompatible material, encasing the enclosed portion of the tab within a polymeric material, thereby producing a trial implant in the form of a body as described above. In accordance with other embodiments of the third aspect, the method may further include the step of providing an attachment means to the exposed portion of the tab.

BRIEF DESCRIPTION OF THE DRAWINGS

A more complete appreciation of the subject matter of the present invention and the various advantages thereof can be realized by reference to the following detailed description in which reference is made to the accompanying drawings in which.

DETAILED DESCRIPTION

As used herein, when referring to bones or other parts of the body, the term "proximal" means closer to the heart and the term "distal" means more distant from the heart. The term "inferior" means toward the feet and the term "superior" means towards the head. The term "anterior" means towards the front part of the body or the face and the term "posterior" means towards the back of the body. The term "medial" means toward the midline of the body and the term "lateral" means away from the midline of the body.

Although the background of the invention section sets forth a discussion of a typical knee joint operation, it is understood that drawbacks associated with existing implants and surgical procedures are applicable to other joints in the human body, including the shoulder and the hip. Although the following description will generally be set forth in connection with knee joint implants and procedures, it is to be understood that the present invention is applicable to other such joints. For instance, the trials discussed herein could be modified for use in the hip or shoulder.

Referring to the drawings, wherein like reference numerals refer to like elements, FIGS. 1-7 depict an embodiment of a tibial trial implant 100 having a body 102 and a tab 104. A kit may be provided including a plurality of trial implants of incrementally different shapes and sizes with respect to implant 100.

As depicted in FIGS. 1-9, body 102 is sized to closely approximate the dimensions of a tibial condyle, and therefore a permanent tibial implant to be surgically implanted. Body 102 includes a medial edge 108, a lateral edge 110, a posterior edge 112, anterior edges 114 and 116, and a recess 120. Recess 120 is positioned between anterior edges 114 and 116. Medial edge 108 is substantially straight, but can be configured differently according to either the natural geometry of the anatomy or according to a surgical cut made therein. Lateral edge 110, posterior edge 112, and anterior edges 114 and 116 are generally curved according to the natural geometry of a tibial condyle. Edges 108, 110, 112, 114, and 116 combine to form a substantially continuous edge, with the edges of recess 120 completing the boundaries of the implant. Edges 108, 110, 112, 114, and 116 and recess 120 may be rounded in a proximal-distal direction in order to prevent sharp angles or corners from being present in implant 100 and causing damage to the patient during insertion and/or extraction thereof. Body 102 also includes a top surface 124 and a bottom surface 126. Top surface 124 includes a bearing portion 118 that may be concave or any other surface suitable to allow smooth articulation with that of a corresponding femoral trial implant. Body 102 is preferably constructed of a polymeric material, such as an ultra-high molecular weight polyethylene (UHMWPE).

It is to be understood that the specific configuration of body 102 may vary in accordance with the present invention. For instance, the design shown in the figures is meant for placement over one side of the resected tibia. A trial implant meant for placement over the other side of the resected tibia may be a mirror image of the design shown in the drawings. Likewise, other embodiments in accordance with the present invention may include differently shaped edges, top and bottom surfaces, and/or recesses.

Tab 104 is disposed within body 102 and extends into recess 120, and is preferably constructed of metal or a similar rigid, biocompatible material of increased hardness and/or durability as compared to the material used to construct body 102. An anterior edge 122 of tab 104 is preferably spaced posteriorly from anterior edges 114 and 116 of body 102 in order to shield tab 104 from contact with the patient. Likewise, an upper surface 128 of tab 104 is preferably spaced distally from top surface 124 of body 102, and a lower surface 130 of tab 104 is preferably spaced proximally from bottom surface 126 of body 102. Therefore, while tab 104 extends into recess 120, it is preferably wholly contained within recess 120 such that it does not extend beyond any of the aforementioned edges or surfaces of body 102. It is within the scope of the present invention for tab 104 to extend beyond top surface 124, bottom surface 126, and/or anterior edges 114 and 116 as may be desirable for the particular surgical procedure or intended use of implant 100. The configuration of tab 104 and recess 120 may preferably take into account the approximate size of a surgical tool, such as a needle driver, hemostat, or other clamping device, and the desire to avoid or substantially eliminate any unintentional contact between the surgical tool and the patient's anatomy surrounding the implantation site.

Tab 104 is understood to comprise both an exposed portion 134 (FIG. 7) disposed within recess 120, and an enclosed portion 132 (FIG. 7) disposed within body 102. Thus, although tab 104 is only accessible by a tool at exposed portion 134, enclosed portion 132 may extend between recess 120 and any edge of body 102. By way of example, one embodiment of enclosed portion 132 is outlined by phantom lines in FIG. 7. Of course, enclosed portion 132 can be of any size and shape that fits within body 102. The greater the size of enclosed portion 132, the more fixed and secure tab 104 is with respect to body 102. Moreover, the greater the size of enclosed portion 132, the stronger the overall construct of implant 100 is.

Tab 104 further defines a hole 106 so that tab 104 may be adaptable with a surgical clamping tool, such as a Kocher, Adson, or other forceps or a Nerve Hook, to provide additional security. Hole 106 can take on any size and is restricted only by the dimensions of recess 120 and anterior edge 122 of tab 104. A variation of hole 106 may include a break in anterior edge 122 of tab 104 such that hole 106 is open in an anterior direction. In such a configuration, hole 106 may be shaped as an "L", for example, and a tool such as a hook may access and manipulate implant 100 by being inserted into hole 106 in a posterior direction around what remains of anterior edge 122. Although hole 106 is located in exposed portion 134, enclosed portion 132 may also include one or more holes or roughened areas to enhance the attachment bonds between tab 104 and body 102. Furthermore, tab 104 may include a lip or at least one protrusions extending proximally from upper surface 128 and/or distally from lower surface 130. The lip and/or protrusion(s) would provide a non-uniform surface and a posterior-facing surface of tab 104 in order to enhance its attachment to a tool during manipulation of implant 100.

Tab 104 is included in implant 100 to provide a surface with which a surgical clamping tool may interact. The existence of tab 104 prevents body 102 from being damaged by such a tool, as the aggressive mating surfaces of surgical tools would otherwise tend to accelerate the deterioration of the polymeric material making up body 102. As such, tab 104 is comprised of materials that provide increased strength, wear resistance, and longevity. Thusly, the effective life of implant 100 extends beyond those of existing trial implants. Tab 104 further acts to more evenly distribute loads encountered by implant 100 from the surgical tools.

Figure 1:
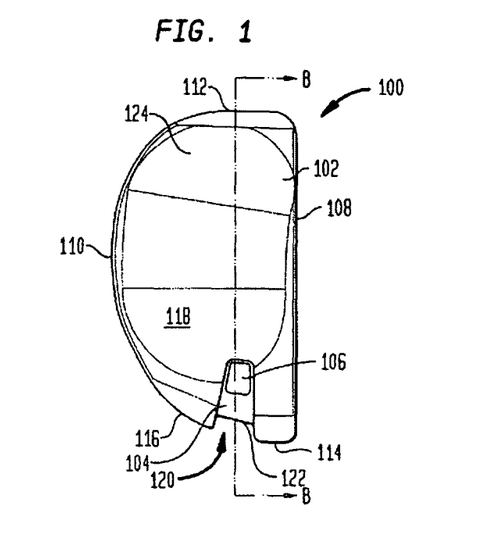
FIG. 1 is a top view of a tibial trial implant in accordance with an embodiment of the present invention.
Figure 2:
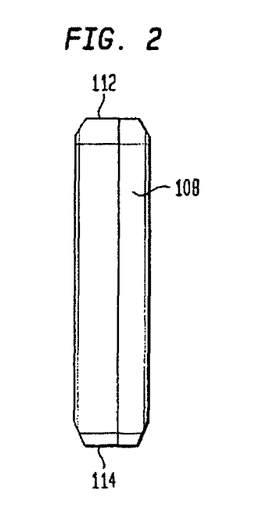
FIG. 2 is a medial-side view of the trial implant as shown in FIG. 1.
Figure 3:
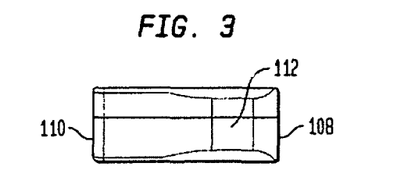
FIG. 3 is a posterior-side view of the trial implant as shown in FIG. 1.
Figure 4:
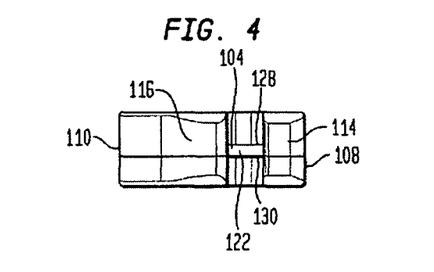
FIG. 4 is an anterior-side view of the trial implant as shown in FIG. 1.
Figure 5:
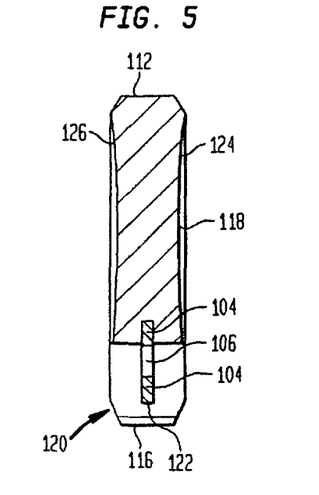
FIG. 5 is a sectional view taken along line B-B of the trial implant as shown in FIG. 1.
Figure 6:
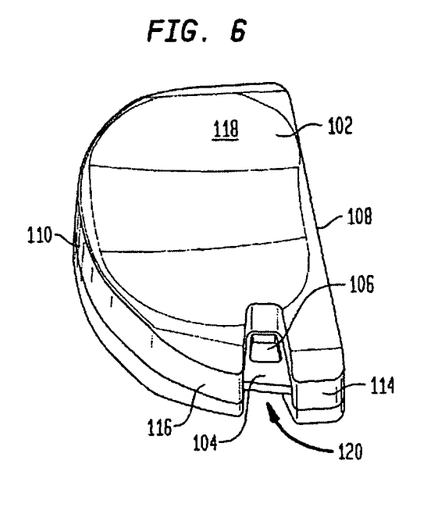
FIG. 6 is an oblique isometric view of the trial implant as shown in FIG. 1.
Figure 7:
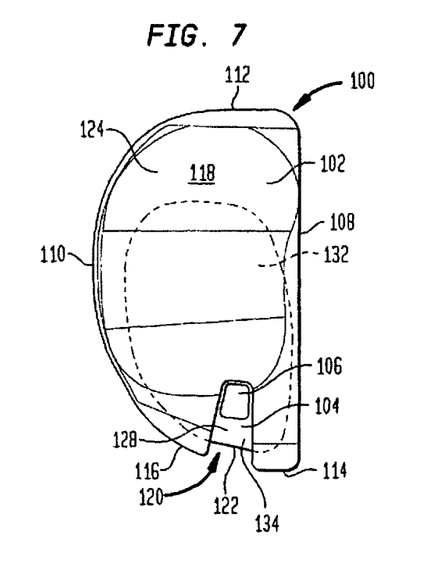
FIG. 7 is an enlarged plan view of the trial implant as shown in FIG. 1 including a phantom line depicting certain internal components of the implant.

Implant 100 is depicted in FIGS. 1 and 7 in an orientation for use on a medial tibial platform of a left knee or a lateral tibial platform of a right knee. Although not shown, bottom surface 126 of implant 100 preferably contains a bearing portion similar to bearing portion 118. Such a construction allows implant 100 to be inverted to include a mirror image of implant 100 as it is depicted in FIGS. 1-7. Thusly, implant 100 preferably includes a symmetric design to allow for use in both left and right knees in either the medial or lateral compartments thereof. This configuration is advantageous in that a surgeon may simply select one tibial trial implant 100 for use with any of the four tibial condyles during surgery.

Of course, implant 100 may alternately be designed for use only in the orientation depicted in FIGS. 1-7. In such a design, bottom surface 126 may be flat or otherwise differently shaped in accordance with the natural geometry of the resected tibial platform. Bottom surface 126 may additionally include a finish that would inhibit movement of the implant with respect to the tibia when placed against the tibial platform. A kit in accordance with such a design may include a pair of implants 100 for each particular size and orientation that are mirror images of one another.

Figure 8:
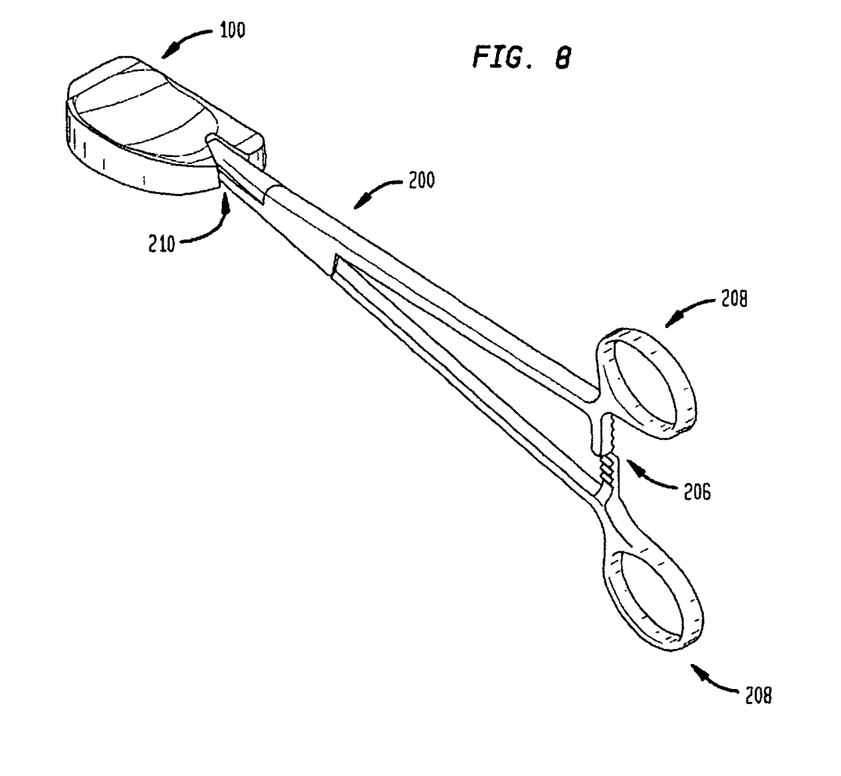
FIG. 8 is a perspective view of the trial implant as shown in FIG. 1 engaged with a tool.
Figure 9:
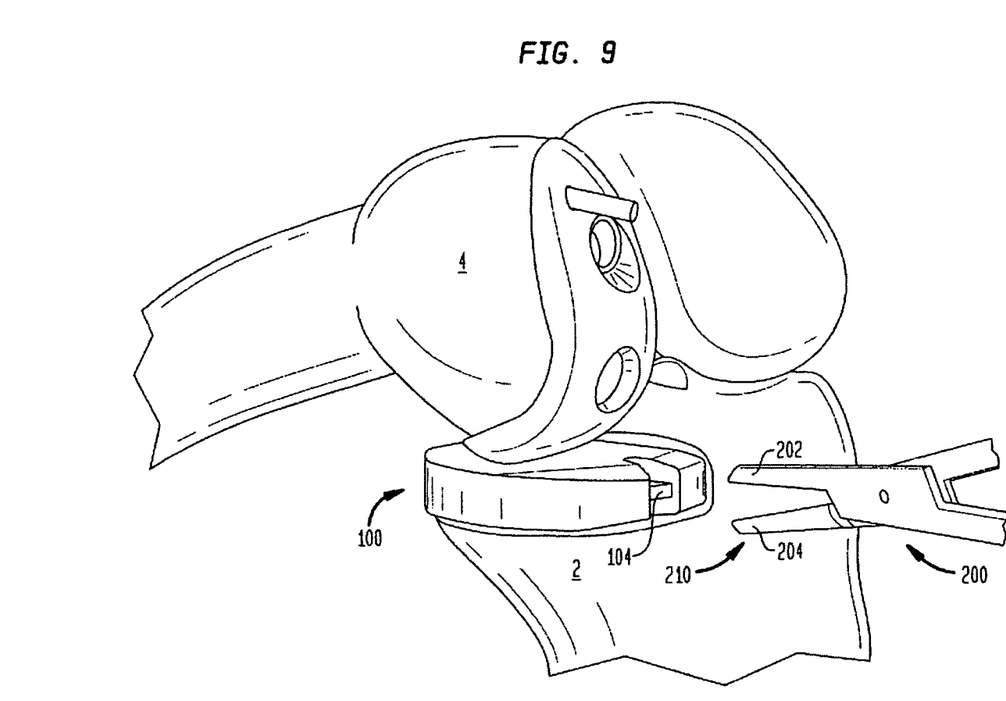
FIG. 9 is an oblique isometric view of the trial implant as shown in FIG. 1 placed during a surgical procedure.
Figure 12:
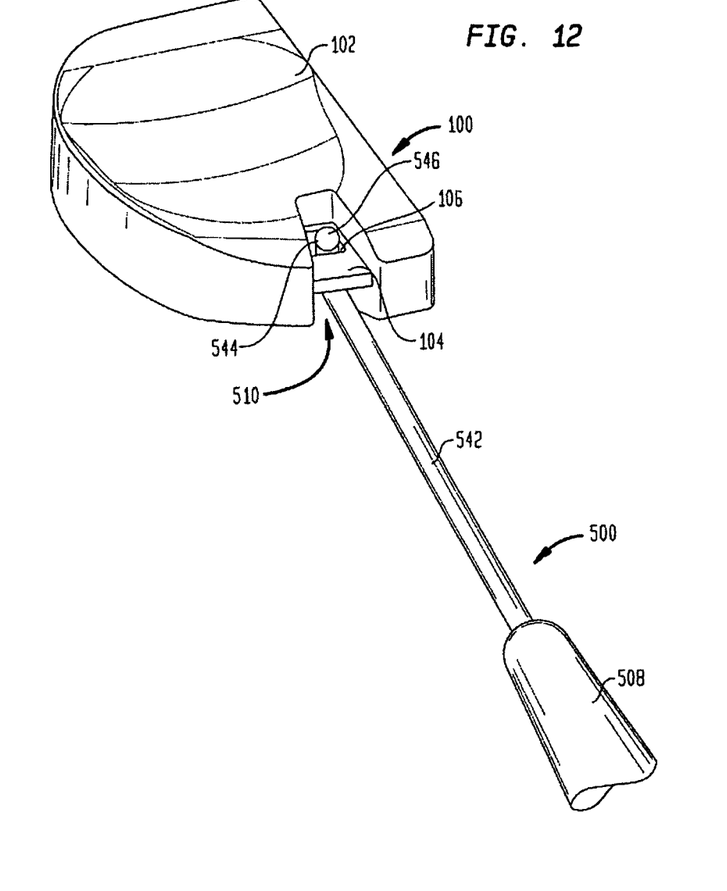
FIG. 12 is another perspective view of the trial implant as shown in FIG. 1 engaged with a tool.

In use, implant 100 may be manipulated as shown in FIGS. 8 and 9. A surgeon first selects an appropriately sized implant 100 from a kit as described above, either by hand or through the use of a tool. Indicia used to label implant 100 may aid the surgeon by providing a reference for each implant and distinguishing between same. The surgeon may base such selection on a predetermined calculation of the size and orientation of the tibial bone, or alternatively according to the immediate results of the surgical procedure. Once the appropriate implant 100 is selected, the surgeon holds a handle 208 of a tool 200 (a needle driver as shown in FIG. 8) to attach to tab 104 between a first arm 202 and a second arm 204. The portions of first arm 202 and second arm 204 that interact with tab 104 make up an attachment portion 210 of tool 200. Attachment portion 210 may be used to attach, grasp, clamp, hook, etc. to implant 100. For example, FIG. 12 depicts another embodiment of a tool 500 including a handle 508 connected by a shaft 542 to an attachment portion 510. Attachment portion 510 includes a hook 544 that attaches to hole 106 of tab 104. A spherical portion 546 is provided at the end of hook 544 to provide greater security between tool 500 and implant 100.

The surgeon then begins the trialing stage of the surgical procedure, during which a "trial and error" process is conducted by using various trial implants to assess the accuracy of the tibio-femoral tracking as well as tibial plateau coverage. The initially selected implant 100 is inserted into the knee joint onto a resected tibial platform and its fit is evaluated. Implant 100 is subsequently extracted from the knee joint, and a different trial implant may be selected and inserted based on the initial evaluation. This process may be repeated using different trial implants until the surgeon is satisfied that a proper selection has been made. While implant 100 is disposed within the knee joint, the knee joint may be manipulated as the surgeon more thoroughly assesses the fit of implant 100 in a dynamic environment. This preferably includes articulating the femur or a femoral trial implant with respect to the tibial trial implant. After determining that implant 100 is of the size and shape appropriate for permanent implantation, the surgeon obtains a permanent tibial implant of corresponding size and shape for subsequent insertion into the knee joint.

Preferably, attachment portion 210 of tool 200 is dimensioned to be substantially contained within recess 120. More preferably, attachment portion 210 is dimensioned to be wholly contained within recess 120 such that attachment portion 210 does not extend beyond top surface 124 or bottom surface 126 of body 102. Such a configuration will substantially eliminate or entirely avoid any unintentional contact between the surgical tool and the patient's anatomy surrounding the implantation site. Of course, the same is applicable to attachment portion 510 of tool 500, or to any tool used with an implant according to the present invention.

It is noted that tools 200 and 500 are only examples of surgical tools. Their detail is depicted and described only to more fully explain the method of using an implant according to the present invention, such as implant 100. Advantageously, any common surgical clamping tool, such as a hemostat, needle driver, clamp, forceps, a Nerve Hook, or the like, may be used that provides the ability to adequately attach to and manipulate implant 100 during surgery. Moreover, the tool need not be designed for surgical use. A standard pair of pliers or the like might suffice. The tool need only be capable of attaching to tab 104 in a secure manner and in such a way that the surgeon may manipulate implant 100 in conjunction with a knee joint, or any other applicable joint in the human body. As a dedicated tool is not required, it is likely that a surgeon will already possess at least one appropriately sized tool and will not have to bear the expense of obtaining a dedicated tool designed solely for use with implant 100. In a typical surgical procedure, there are a plurality of generic surgical tools such that a substitute tool is readily available should the primary tool be rendered non-sterile due to drop or contamination. Thus, the size, weight, and cost associated with a kit in accordance with the present invention are reduced. However, while a kit according to the present invention is designed to employ the use of a standard tool for at least the aforementioned reasons, a dedicated tool could certainly be developed for use with same.

Certain desirable features of tools 200 and 500 are herein described, although none is necessarily required. An additional feature of tool 200 that may be advantageous is that it may include a releasable clasp mechanism 206 which allows tool 200 to maintain its attachment to implant 100 after the surgeon has released handle 208. During manipulation of the knee joint while implant 100 is disposed therein, tool 200 can remain attached or may be removed.

Implant 100 is constructed by first fabricating tab 104 to the desired dimensions by cutting, stamping, or any other appropriate manufacturing method. Depending on the material used, tab 104 may also be molded. Tab 104 is then at least partially encased within body 102 through molding, gluing, press-fitting, and/or welding. In one embodiment, the polymeric material of body 102 is molded around tab 104 to form implant 100. This process is often referred to as overmolding. During the molding process, an enclosure is provided which secures tab 104 and provides a negative of body 102. The polymeric material is heated to its flowable state and injected into the enclosure such that any or all of the above-mentioned features of body 102 are formed. The polymeric material is only molded around enclosed portion 132, thereby creating recess 120 and leaving exposed portion 134 unconcealed by the polymeric material. The polymeric material is then allowed to cool such that body 102 maintains its molded form. In an alternative embodiment, two halves of body 102 adjacent top surface 124 and bottom surface 126, respectively, may be molded or machined separately and thereafter assembled about tab 104 by gluing, press-fitting, and/or welding the halves together. Body 102 may subsequently be filed or polished to remove any sharp edges or corners or any excess polymeric material left from the molding process. Hole 106 of tab 104 can be cut, punched, or formed in any other like manner either before or after body 102 is molded around tab 104. A finish may additionally be applied to top surface 124 and/or bottom surface 126 to increase biocompatibility, wear, traction, or any other desirable feature of implant 100.

Implant 100 is depicted in certain Figures as including indicia. It may be desirable to provide such indicia on any of the external surfaces of implant 100 to denote information pertaining to size, material, part number, or any other relevant feature. It may also be desirable to mark implant 100 with "TRIAL DO NOT IMPLANT" or a similar phrase so that same is not mistakenly confused with a permanent tibial implant. Indicia may be added to implant 100 by appropriately altering the enclosure used during the molding process of body 102, or may alternately be written, etched, scribed, branded, or marked in any other known fashion onto body 102 after its construction. Indicia may also be provided on tab 104, although it may become distorted or altered during the life of implant 100.

It is within the scope of the present invention for implant 100 to be sized and shaped to approximate any or all of the components of a permanent tibial implant. In an embodiment, implant 100 may approximate the combination of both a base plate and an insert of a permanent tibial implant. As such, implant 100 may be placed directly against the resected tibial platform and articulate with the corresponding femoral bone so that the final height and orientation of both the base plate and the insert can be appreciated.

In another embodiment, implant 100 may be sized to closely approximate the dimensions of an insert of a permanent tibial implant, whereby a permanent base plate may be implanted in a patient and one or more implants 100 may be utilized in a trialing procedure in order to select an appropriate permanent insert. Of course, yet another embodiment would include a similar procedure whereby one or more implants 100 resembling a permanent base plate may be utilized in a trialing procedure with a permanent insert. Moreover, a kit in accordance with the present invention may include a plurality of implants 100 of incrementally different shapes and sizes with respect to a base plate, an insert, and/or a combination thereof.

As implant 100 is sized to closely approximate the dimensions of a tibial condyle as viewed in the distal direction, it is within the scope of the present invention to provide implant 100 as an approximation of either one or both of the tibial condyles. Therefore, implant 100 may resemble either the medial or lateral tibial condyle, or may be configured to approximate the entire proximal end of the tibia taking into account both the medial and lateral tibial condyles.

Figure 10:
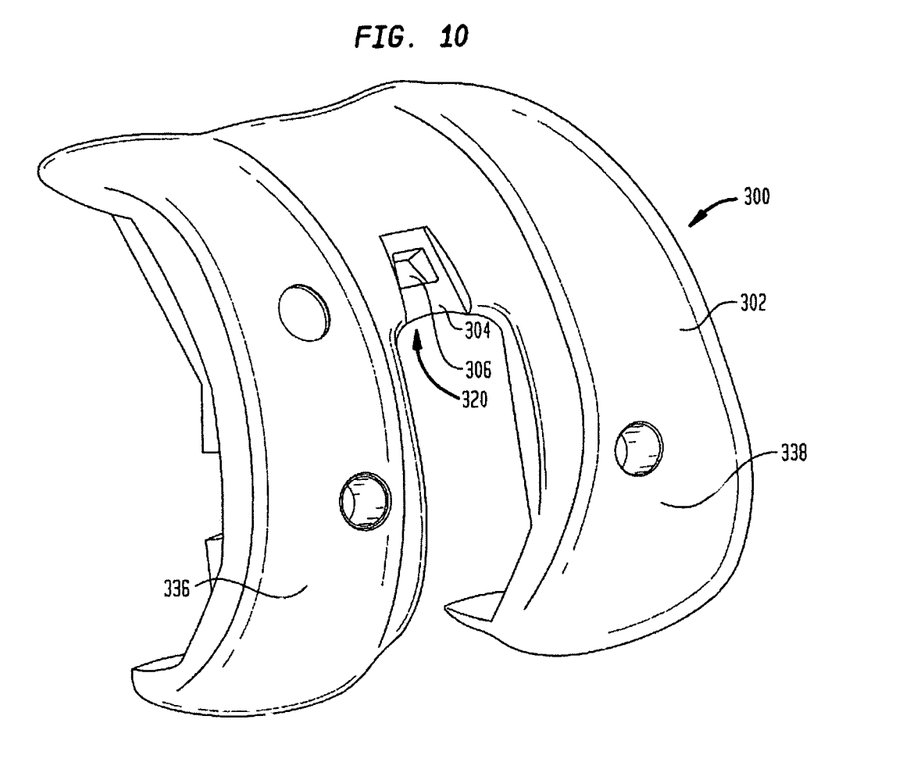
FIG. 10 is an oblique isometric view of a femoral trial implant in accordance with another embodiment of the present invention.

Although implant 100 has been described and depicted within regard to a tibia, the configuration of implant 100 could be adapted to aid in trialing procedures with respect to other bones and/or joints. Thus, while it has been repeatedly described that implant 100 can be differently sized and shaped so that more than one configuration of implant 100 can be utilized in a trialing procedure with respect to the tibial component of a knee joint, other implants may be constructed in accordance with the present invention. For example, FIG. 10 depicts an embodiment of a femoral trial implant 300 having a body 302 and a tab 304. Body 302 is generally comprised of a first condyle 336 and a second condyle 338 which act as bearing surfaces. Disposed between first and second condyles 336 and 338 is tab 304 within a recess 320 formed in body 302. Tab 304 includes a hole 306. Implant 300 is depicted as a femoral trial implant, which includes first and second compartments as first and second condyles 336 and 338 and a third compartment as a patellar track disposed therebetween. It is within the scope of the present invention to provide a trial implant including one or more of the aforementioned compartments.

Figure 11:
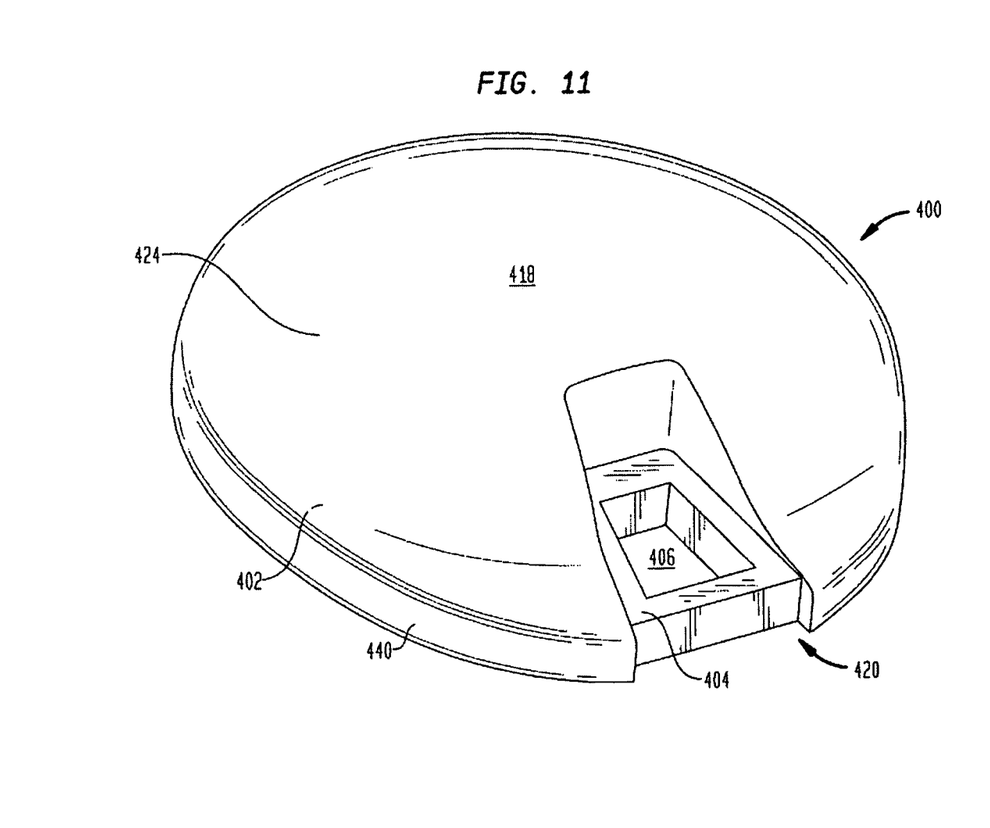
FIG. 11 is an oblique isometric view of a patellar trial implant in accordance with yet another embodiment of the present invention.

In another embodiment, FIG. 11 depicts a patellar trial implant 400 having a body 402 and a tab 404. Body 402 includes a top surface 424 having a bearing surface 418, and an edge 440 defining a recess 420 which contains tab 404. Tab 404 includes a hole 406. Of course, implants 300 and 400 may include any or all of the features described above with respect to implant 100. Furthermore, a kit may be provided including a plurality of trial implants of incrementally different shapes and sizes with respect to implant 300 or 400.

Therefore, it is contemplated that the configuration of an implant according to the present invention could be adapted to approximate any other bone that is part of a joint, such as the shoulder or hip, where a surgical procedure relating to such joint may require or benefit from a trialing procedure.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A trial implant comprising:
    a body sized to closely approximate the dimensions of a permanent tibial implant to be surgically implanted, the body having a continuous edge, the continuous edge defining a recess, the body being composed of a first material;
    a tab composed of a second material that is more durable than the first material;
    wherein a majority of the tab is encased within the body and an exposed portion of the tab extends into the recess.

2. A trial implant comprising:
    a body sized to closely approximate the dimensions of a permanent femoral implant to be surgically implanted, the body having a continuous edge, the continuous edge defining a recess, the body being composed of a first material;
    a tab composed of a second material that is more durable than the first material;
    wherein a majority of the tab is encased within the body and an exposed portion of the tab extends into the recess.

3. A trial implant comprising:
    a body sized to closely approximate the dimensions of a permanent patellar implant to be surgically implanted, the body having a continuous edge, the continuous edge defining a recess, the body being composed of a first material;
    a tab composed of a second material that is more durable than the first material;
    wherein a majority of the tab is encased within the body and an exposed portion of the tab extends into the recess.

4. A trial implant comprising:
    a body sized to closely approximate the dimensions of a permanent implant to be surgically implanted, the body having a top surface defining a top bearing portion, a bottom surface defining a bottom bearing portion, and a continuous edge defining a recess, the body being composed of a first material;
    a tab composed of a second material that is more durable than the first material;
    wherein an enclosed portion of the tab is encased within the body and an exposed portion of the tab extends into the recess, and
    wherein a contour of the top bearing portion is a mirror image of a contour of the bottom bearing portion.

5. The trial implant of claim 4 wherein the exposed portion of the tab is wholly contained within the recess.

6. The trial implant of claim 4 wherein the first material is a polymeric material and the second material is a rigid biocompatible material.

7. The trial implant of claim 6 wherein the rigid biocompatible material is metal.

8. The trial implant of claim 4 wherein the continuous edge includes upper and lower rounded portions proximal to the top surface and the bottom surface, respectively.

9. The trial implant of claim 4 wherein the tab includes an attachment means.

10. The trial implant of claim 9 wherein the attachment means is a hole.

11. The trial implant of claim 9 wherein the attachment means is a lip.

12. The trial implant of claim 9 wherein the attachment means is at least one protrusion.

13. The trial implant of claim 4 wherein the implant is marked with indicia.

14. A method of performing a trialing procedure comprising the steps of:
    providing a trial implant including a body and a tab, the body being sized to closely approximate the dimensions of a permanent implant to be surgically implanted, the body having a top surface defining a top bearing portion, a bottom surface defining a bottom bearing portion, and a continuous edge defining a recess, the body being composed of a first material, the tab composed of a second material that is more durable than the first material, wherein an enclosed portion of the tab is encased within the body and an exposed portion of the tab extends into the recess, and wherein a contour of the top bearing portion is a mirror image of a contour of the bottom bearing portion;
    attaching a tool to the tab;
    inserting the implant onto a resected joint surface;
    evaluating the implant with respect to the joint surface; and
    extracting the implant.

15. The method of claim 14 wherein the joint is a knee joint.

16. The method of claim 14
    wherein the first material is a polymeric material and the second material is a rigid biocompatible material.

17. The method of claim 14 wherein the step of providing a trial implant further includes:
    providing a kit including a plurality of implants of incrementally different shapes and sizes; and
    selecting one of the plurality of implants.

18. The method of claim 17 wherein after the step of extracting, the method further comprises the steps of:
    selecting a second implant from the plurality of implants;
    attaching the tool to the tab of the second implant;
    inserting the second implant onto the resected joint surface;
    evaluating the second implant with respect to the joint surface; and
    extracting the second implant.

19. The method of claim 14 wherein after the step of extracting, the method further comprises the step of selecting a permanent implant corresponding to the trial implant.

20. The method of performing a trialing procedure of claim 14 wherein the step of providing a trial implant includes the body being sized to closely approximate the dimensions of a permanent tibial implant.

21. The method of performing a trialing procedure of claim 14 wherein the step of providing a trial implant includes the body being sized to closely approximate the dimensions of a permanent femoral implant.

22. The method of performing a trialing procedure of claim 14 wherein the step of providing a trial implant includes the body being sized to closely approximate the dimensions of a permanent patellar implant.

23. The method of claim 14 wherein the step of attaching the tool to the tab further includes utilizing a tool having an attachment portion that is dimensioned to be substantially contained within the recess.

24. The method of claim 14
wherein the step of attaching the tool to the tab further includes utilizing a tool having an attachment portion that is dimensioned to be wholly contained within the recess such that the attachment portion does not extend beyond the top surface or the bottom surface of the body.

25. A kit comprising:
a plurality of trial implants of incrementally different shapes and sizes, each implant having:
  a body sized to closely approximate the dimensions of a permanent implant to be surgically implanted, the body having a top surface defining a top bearing portion, a bottom surface defining a bottom bearing portion, and a continuous edge defining a recess, the body being composed of a first material; and
  a tab composed of a second material that is more durable than the first material;
  wherein an enclosed portion of the tab is encased within the body and an exposed portion of the tab extends into the recess, and
  wherein a contour of the top bearing portion is a mirror image of a contour of the bottom bearing portion.

26. The kit of claim 25 wherein the exposed portion of the tab is wholly contained within the recess.

27. The kit of claim 25 further including a tool having an attachment portion configured for attachment to the exposed portion of the tab.

28. The trial implant of claim 27 wherein the attachment portion is a clamping portion.

29. The trial implant of claim 27 wherein the attachment portion is a hooking portion.

30. The kit of claim 27 wherein the attachment portion is dimensioned to be substantially contained within the recess.

31. The kit of claim 27
wherein the attachment portion is dimensioned to be wholly contained within the recess such that the attachment portion does not extend beyond the top surface or the bottom surface of the body.

32. The kit of claim 27 wherein the tab includes an attachment means.

33. A method of making a trial implant comprising the steps of:
providing a tab made of a rigid biocompatible material;
encasing an enclosed portion of the tab within a polymeric material, thereby producing a trial implant in the form of a body sized to closely approximate the dimensions of a permanent implant to be surgically implanted, the body having a top surface defining a top bearing portion, a bottom surface defining a bottom bearing portion, and a continuous edge defining a recess, an exposed portion of the tab extending into the recess;
wherein the rigid biocompatible material is more durable than the polymeric material, and
wherein a contour of the top bearing portion is a mirror image of a contour of the bottom bearing portion.

34. The method of making a trial implant of claim 33 further including the step of providing an attachment means to the exposed portion of the tab.

* * * * *